(12) United States Patent
Lee et al.

(10) Patent No.: US 10,517,551 B2
(45) Date of Patent: Dec. 31, 2019

(54) X-RAY PHOTOGRAPHING APPARATUS AND METHOD

(71) Applicant: OSSTEMIMPLANT CO., LTD., Seoul (KR)

(72) Inventors: Dong Yul Lee, Incheon (KR); Jae Hee Woo, Suwon-si (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 206 days.

(21) Appl. No.: 15/745,641

(22) PCT Filed: Jul. 12, 2016

(86) PCT No.: PCT/KR2016/007545
§ 371 (c)(1),
(2) Date: Jan. 17, 2018

(87) PCT Pub. No.: WO2017/014476
PCT Pub. Date: Jan. 26, 2017

(65) Prior Publication Data
US 2018/0206801 A1    Jul. 26, 2018

(30) Foreign Application Priority Data

Jul. 17, 2015  (KR) .......................... 10-2015-0101741

(51) Int. Cl.
*A61B 6/03*   (2006.01)
*A61B 6/14*   (2006.01)
*A61B 6/00*   (2006.01)

(52) U.S. Cl.
CPC .............. *A61B 6/14* (2013.01); *A61B 6/4441* (2013.01); *A61B 6/588* (2013.01)

(58) Field of Classification Search
CPC ......... A61B 6/14; A61B 6/588; A61B 6/4441; A61B 6/032; A61B 6/4429
See application file for complete search history.

(56) References Cited

U.S. PATENT DOCUMENTS 10,265,033 B2 *   4/2019  Lim ....................... A61B 6/035

FOREIGN PATENT DOCUMENTS

JP   2007-526103 A    9/2007
JP   2010-512829 A    4/2010
(Continued)

*Primary Examiner* — Don K Wong
(74) *Attorney, Agent, or Firm* — Novick, Kim & Lee, PLLC; Sang Ho Lee

(57) ABSTRACT

The present invention relates to an X-ray photographing apparatus and method capable of variously and finely adjusting a magnification power by sliding a rotating portion supporting an X-ray source portion and a sensor portion facing each other in a state in which an interval between the X-ray source portion and the sensor portion is maintained to change an interval between the sensor portion and a head of a subject to be examined. The X-ray photographing apparatus includes: a rotating portion including an X-ray source portion and a sensor portion facing each other and provided at a shaft through a moving means so as to be movable in an X-ray irradiation direction; and an actuating portion adjusting a magnification power by changing an interval between the sensor portion and a head of a subject to be examined in a state in which an interval between the X-ray source portion and the sensor portion is maintained.

20 Claims, 10 Drawing Sheets

(56) References Cited

FOREIGN PATENT DOCUMENTS

| KR | 10-2010-0011300 A | 2/2010 |
|---|---|---|
| KR | 10-2012-0097562 A | 9/2012 |
| KR | 10-1401927 B | 5/2014 |
| KR | 10-1536072 B1 | 7/2015 |

* cited by examiner

X-RAY PHOTOGRAPHING APPARATUS AND METHOD

TECHNICAL FIELD

The present invention relates to an X-ray photographing apparatus and method, and more particularly, to an X-ray photographing apparatus and method capable of variously and finely adjusting a magnification power by sliding a rotating portion supporting an X-ray source portion and a sensor portion facing each other in a state in which an interval between the X-ray source portion and the sensor portion is maintained to change an interval between the sensor portion and a head of a subject to be examined.

BACKGROUND ART

Generally, dental clinics are provided with X-ray photographing apparatuses capable of performing X-ray photographing in order to treat teeth and various periodontal diseases or figure out a state of teeth and an alveolar bone for the purpose of correction of irregularities of the teeth, or the like.

The X-ray photographing apparatus used in the dental clinic transmits a predetermined amount of X-ray through a tooth portion, which is a body portion to be photographed, senses an intensity of the transmitted X-ray, converting the intensity of the transmitted X-ray into an electrical signal corresponding to the intensity of the transmitted X-ray, and transmits the electrical signal to a computer. In this case, the computer calculates intensities of X-rays of the respective points of photographed body portions and processes the intensity to obtain an image.

As the X-ray photographing apparatus described above, an X-ray photographing apparatus for a computerized tomography (CT) capable of photographing a three-dimensional stereoscopic image, an X-ray photographing apparatus for a panorama capable of photographing a two-dimensional plane image, and the like, have been mainly used.

The X-ray photographing apparatus for a CT, which is an imaging apparatus displaying a tomographic image of a human body that may not be displayed by general photographing, is a tomography apparatus transmitting an X-ray through the human body while rotating at a predetermined angle over 360°, collecting the transmitted X-ray through a detector such as a sensor, or the like, and reconfiguring an absorption value for a cross section of the human body to display the reconfigured absorption value as an image.

In addition, the X-ray photographing apparatus for a panorama, which photographs the entirety on the basis of an X-ray generating apparatus in a circumferential direction, is an apparatus capable of performing panorama photographing to view an entire tooth state and a temporomandibular joint at a glance.

However, there is a disadvantage that the X-ray photographing apparatus for a CT may obtain only a CT image and the X-ray photographing apparatus for a panorama may obtain only a panorama image.

In order to solve the problem described above, apparatuses capable of performing both of CT photographing and panorama photographing using one X-ray photographing apparatus have been suggested.

For example, Korean Patent No. 10-1401927 discloses an "X-ray Photographing Apparatus Combining Panorama and CT for Dental Clinic".

In the X-ray photographing apparatus combining panorama and CT for a dental clinic, a panorama sensor and a CT sensor rotate around a concentric axis by a rotation driving portion, such that a mode is switched, and at the time of switching the mode, a rotary arm in which an X-ray light source portion is disposed horizontally moves so as to face an X-ray sensor portion to vary a distance between the X-ray light source portion and the X-ray sensor portion with respect to a subject to be examined, thereby adjusting an image magnification depending on each mode and performing photographing.

However, the X-ray photographing apparatus combining panorama and CT for a dental clinic as described above can not but use only one set panorama image magnification at the time of performing panorama photographing using the panorama sensor, and can not but use only one set CT image magnification also at the time of performing CT photographing using the CT sensor.

That is, since the X-ray photographing apparatus combining panorama and CT for a dental clinic may not finely adjust a magnification power depending on a size of a head of the subject to be examined or a photographing environment and can not but perform photographing by applying only a fixedly set magnification power, quality of an image is significantly deteriorated depending on the size of the head of the subject to be examined.

In addition, the X-ray photographing apparatus combining panorama and CT for a dental clinic is configured in a horizontal moving structure through a ball screw such as a horizontal driving motor, a rotary arm horizontal driving ball screw, a connection shaft fixing member, and the like, and when the rotary arm having a weight of 60 kg or more is horizontally moved through the ball screw, a load of the motor is increased. Therefore, a motor having a high capacity should be used. As a result, an entire weight of the rotary arm is increased, such that a volume of the rotary arm is increased, and a rotation driving force of the connection shaft connected to the rotary arm is increased.

DISCLOSURE

Technical Problem

An object of the present invention is to provide an X-ray photographing apparatus and method capable of variously and finely adjusting a magnification power by sliding a rotating portion supporting an X-ray source portion and a sensor portion facing each other in a state in which an interval between the X-ray source portion and the sensor portion is maintained to change an interval between the sensor portion and a head of a subject to be examined.

Another object of the present invention is to provide an X-ray photographing apparatus and method in which an actuating portion configured to include a rotating unit, a link unit, and a driving unit may slide a rotating portion through a simple link structure to allow a magnification power to be easily adjusted, such that the rotating portion having a significant weight is slid in a link manner to reduce a load of the driving unit, thereby reducing an entire volume of the rotating portion to compactly configure the rotating portion.

Technical Solution

According to an aspect of the present invention, an X-ray photographing apparatus includes: a rotating portion including an X-ray source portion and a sensor portion facing each other and provided at a shaft through a moving means so as to be movable in an X-ray irradiation direction; and an actuating portion adjusting a magnification power by changing an interval between the sensor portion and a head of a subject to be examined in a state in which an interval between the X-ray source portion and the sensor portion is maintained.

The actuating portion may adjust the magnification power to a provisional magnification power by changing the interval between the sensor portion and the head of the subject to be examined into a preset interval, and then adjust the magnification power to a final magnification power by changing the interval between the sensor portion and the head of the subject to be examined so as to become wide or narrow in consideration of a size of the head of the subject to be examined.

The actuating portion may adjust the magnification power by moving the rotating portion so that the rotating portion moves to and is positioned at any one of one side position, the other side position, and an intermediate position corresponding to any position in a section between one side position and the other side position.

The actuating portion may change the interval between the sensor portion and the head of the subject to be examined so that the magnification power is adjusted to a magnification power for panorama photographing or a magnification power for computerized tomography (CT) photographing.

The actuating portion may change the interval between the sensor portion and the head of the subject to be examined so that the magnification power is adjusted to any one of a plurality of panorama photographing magnification powers.

The actuating portion may change the interval between the sensor portion and the head of the subject to be examined so that the magnification power is adjusted to any one of a plurality of CT photographing magnification powers.

The sensor portion may be configured to perform panorama photographing or CT photographing.

The moving means may be configured so that the rotating portion is relatively movable with respect to the shaft.

The moving means may be configured to include a fixed plate provided at the shaft, guide rails provided on any one of one side of the fixed plate and one side of an inner portion of the rotating portion, and guide blocks provided on the other of one side of the fixed plate and one side of the inner portion of the rotating portion and rail-coupled to the guide rails.

The guide blocks may be provided on both sides of an upper surface of the fixed plate, the guide rails may be provided on one side of the inner portion of the rotating portion corresponding to both sides of the upper surface of the fixed plate, and step portions extended in a length direction so that the guide blocks are mounted thereon may be formed on both sides of the upper surface of the fixed plate.

The actuating portion may be configured to include: a rotating unit provided in the rotating portion; a link unit having one end connected to one point on a radius of rotation of the rotating unit in a hinge manner and the other end connected to one point of the moving means in a hinge manner; and a driving unit rotating the rotating unit.

The rotating unit may be configured to include a first gear, and the driving unit may be configured to include a second gear engaged with the first gear.

The rotating unit may be configured to include a sensing bracket provided at one side thereof and a sensing sensor sensing a rotation position of the sensing bracket depending on rotation of the rotating unit.

The rotating unit may be configured to include an angle limiting stopper provided at one side thereof and a C-shaped groove portion formed at a portion of the rotating portion corresponding to the angle limiting stopper.

An elastic member elastically pulling the fixed plate toward the X-ray source portion may be provided.

The link unit may be provided with a length adjusting portion.

One side of the link unit may be bent in a semi-circular shape.

The link unit may be configured to include: a first body connected to one point on the radius of rotation of the rotating unit in the hinge manner; a second body connected to one point of the moving means in the hinge manner; and a length adjuster having one end fastened to the first body in a left-handed or right-handed manner and the other end fastened to the second body in an opposite manner to that of the first body and adjusting a distance between the first body and the second body.

The rotating portion may be configured to include an upper frame provided with a rectangular hole through which the shaft penetrates and a lower frame covering a lower portion of the upper frame, and the actuating portion may be configured to include a rotating unit provided on a hollow hole formed in one side of the rotating portion, a link unit having one end connected to one point on a radius of rotation of the rotating unit in a hinge manner and the other end connected to one point of the moving means in a hinge manner, and a driving unit rotating the rotating unit.

The rotating unit may be configured to include a bearing mounted on the hollow hole, an upper switching shaft mounted on an inner portion of the bearing, a lower switching shaft mounted beneath the inner portion of the bearing, and a first gear coupled to an upper outer circumferential surface of the upper switching shaft, and the sensor portion may be fixedly mounted at a lower portion of one side of the rotating portion.

According to another aspect of the present invention, an X-ray photographing apparatus includes: an actuating portion adjusting a magnification power by moving a rotating portion supporting an X-ray source portion and a sensor portion facing each other in a state in which an interval between the X-ray source portion and the sensor portion is maintained to change an interval between the sensor portion and a head of a subject to be examined.

The actuating portion may adjust the magnification power to a provisional magnification power by changing the interval between the sensor portion and the head of the subject to be examined into a preset interval, and then adjust the magnification power to a final magnification power by changing the interval between the sensor portion and the head of the subject to be examined so as to become wide or narrow in consideration of a size of the head of the subject to be examined.

According to still another aspect of the present invention, an X-ray photographing method includes: a step of adjusting a magnification power by changing an interval between a sensor portion and a head of a subject to be examined in a state in which an interval between an X-ray source portion and the sensor portion facing each other is maintained.

The step of adjusting the magnification power may include: a first adjusting step of adjusting the magnification power to a provisional magnification power by changing the interval between the sensor portion and the head of the subject to be examined into a preset interval; and a second adjusting step of adjusting the magnification power to a final magnification power by changing the interval between the sensor portion and the head of the subject to be examined so as to become wide or narrow in consideration of a size of the head of the subject to be examined.

The interval between the sensor portion and the head of the subject to be examined may be changed so that the magnification power is adjusted to any one of a magnification power for panorama photographing and a magnification power for CT photographing.

The interval between the sensor portion and the head of the subject to be examined may be changed so that the magnification power is adjusted to any one of a plurality of panorama photographing magnification powers.

The interval between the sensor portion and the head of the subject to be examined may be changed so that the magnification power is adjusted to any one of a plurality of panorama photographing magnification powers.

The sensor portion may perform panorama photographing or CT photographing.

Advantageous Effects

According to the present invention as described above, the magnification power may be variously and finely adjusted by sliding the rotating portion supporting the X-ray source portion and the sensor portion facing each other in a state in which the interval between the X-ray source portion and the sensor portion is maintained to change the interval between the sensor portion and the head of the subject to be examined. Particularly, in switching and adjusting the panorama photographing and the CT photographing, adjusting the magnification power to any one of the plurality of panorama photographing magnification powers, or adjusting the magnification power to any one of the plurality of CT photographing magnification powers, the magnification power may be variously and finely adjusted.

In addition, the actuating portion configured to include the rotating unit, the link unit, and the driving unit may slide the rotating portion through the simple link structure to easily adjust the magnification power. Particularly, a rotating portion having a weight of 60 kg or more may be slid in a link manner to reduce a load of the driving unit, thereby reducing an entire volume of the rotating portion to compactly configure the rotating portion.

In addition, the length adjusting portion may be provided at a central portion of the rotating link to finely adjust interlock between the rotation of the sensor portion and the sliding of the rotating portion.

Further, a gap between the fixed plate and the rotating portion may be prevented through an elastic member elastically pulling the fixed plate toward the X-ray source portion.

Further, a distance between the X-ray source portion and the sensor portion is constantly maintained, but a distance between the sensor portion and the head of the subject to be examined may be changed, such that the magnification power may be adjusted to a magnification power appropriate for panorama image photographing or CT photographing to perform both of the panorama image photographing and the CT photographing.

Further, the distance between the sensor portion and the head of the subject to be examined is changed, thereby making it possible to improve quality of an image at the time of performing panorama photographing.

Further, both of the CT photographing and the panorama photographing may be performed through a simple structure, such that a manufacturing cost may be reduced.

Further, an initial position of the rotating unit may be set through the sensing bracket and the sensing sensor.

Further, excessive rotation of the rotating unit may be prevented through the angle limiting stopper and the C-shaped groove portion.

Further, one side of the link unit is configured to be bent in the semi-circular shape, thereby making it possible to avoid interference with a cable, or the like, connected to the sensor portion.

BEST MODE

Figure 1:
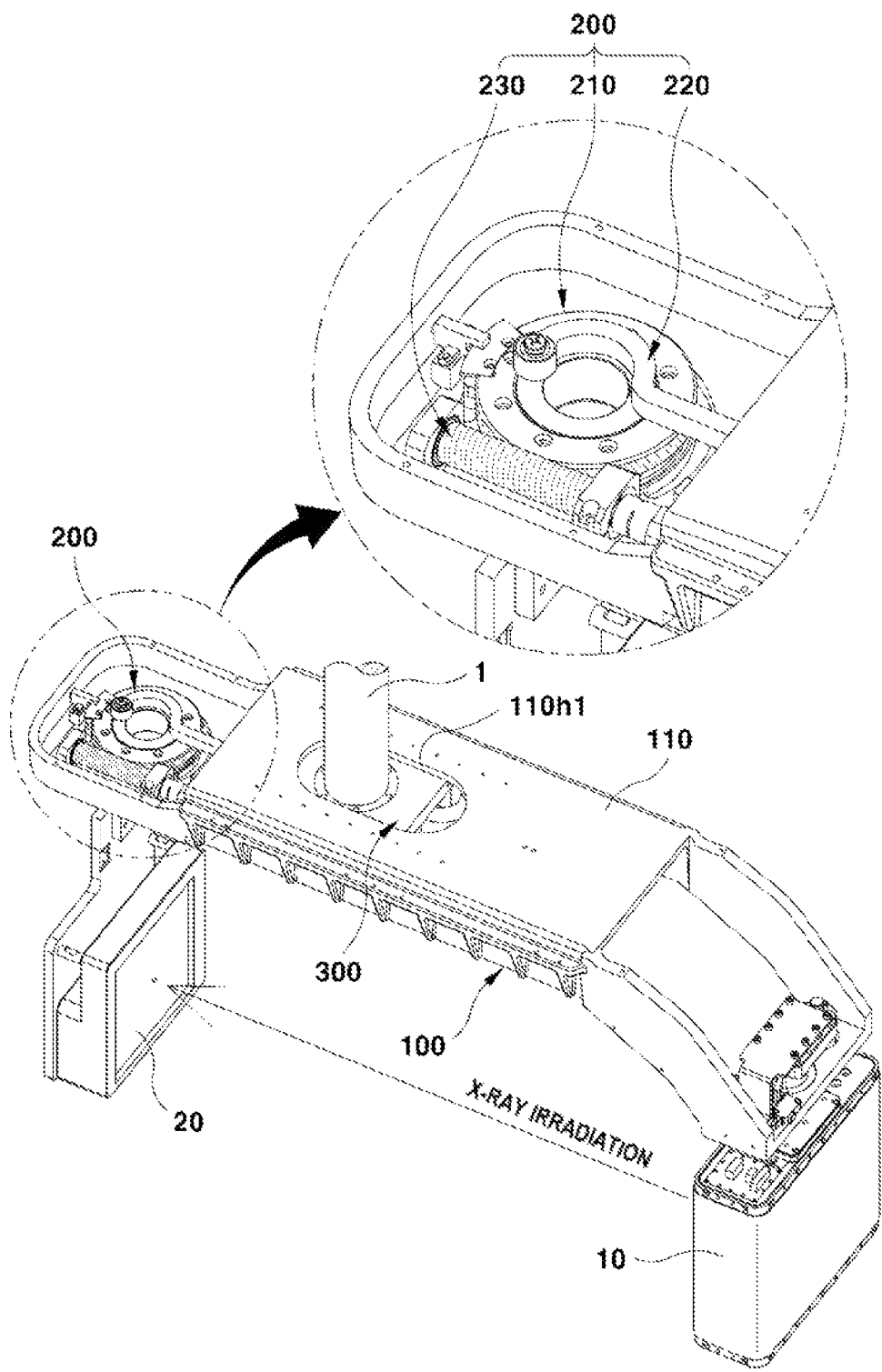
FIG. 1 is a perspective view illustrating an X-ray photographing apparatus according to an exemplary embodiment of the present invention.

The present invention may be implemented in several different forms without departing from the spirit and scope of the present invention. Therefore, exemplary embodiments of the present invention are only examples in all respects, and should not be restrictively interpreted.

Terms used in the specification, 'first', 'second', etc., may be used to describe various components, but the components are not to be interpreted to be limited to the terms.

The terms are used only to distinguish one component from another component. For example, a 'first' component may be called a 'second' component, and the 'second' component may also be called the 'first' component, without departing from the scope of the present invention.

A term 'and/or' includes a combination of a plurality of related items or any one of the plurality of related items.

It should be understood that when one component is referred to as being "connected to" or "coupled to" another component, it may be connected directly to or coupled directly to another component or be connected to or coupled to another component with the other component interposed therebetween.

On the other hand, it should be understood that when one element is referred to as being "connected directly to" or "coupled directly to" another element, it may be connected to or coupled to another element without the other element interposed therebetween.

Terms used in the present specification are used only in order to describe specific exemplary embodiments rather than limiting the present invention. Singular forms are intended to include plural forms unless the context clearly indicates otherwise.

It is to be understood that the terms "include" or "have" used in this specification, specify the presence of stated features, steps, operations, components, parts mentioned in this specification, or a combination thereof, but do not preclude the presence or addition of one or more other features, numerals, steps, operations, components, parts, or a combination thereof.

Unless being defined otherwise, it is to be understood that all the terms used in the present specification including technical and scientific terms have the same meanings as those that are generally understood by those skilled in the art.

It must be understood that the terms defined by the dictionary that is generally used are identical with the meanings within the context of the related art, and they should not be ideally or excessively formally defined unless the context clearly dictates otherwise.

Hereinafter, exemplary embodiments of the present invention will be described in detail with reference to the accompanying drawings. The same reference numerals will be used to describe the same or similar components, independent of the reference numerals and an overlapped description of the same components will be omitted.

When it is determined that the detailed description of the known art related to the present invention may obscure the gist of the present invention, the detailed description thereof will be omitted.

An X-ray photographing apparatus according to an exemplary embodiment of the present invention is configured to include a rotating portion 100 and an actuating portion 200, as illustrated in FIGS. 1 to 4.

First, the rotating portion 100 will be described.

The rotating portion 100, which is a portion extended in an X-ray irradiation direction, is provided with an X-ray source portion 10 and a sensor portion 20 facing each other, and is provided at a shaft 1 through a moving means 300 so as to be slid in the X-ray irradiation direction.

In detail, the sensor unit 20 may be provided to be positioned at a lower portion of one side of the rotating portion 100, and the X-ray source portion 10 may be provided to be positioned at a lower portion of the other side of the rotating portion 100.

The sensor portion 20 may be formed of a sensor capable of performing panorama photographing or computerized tomography (CT) photographing, for example, a common sensor that may be used as a sensor for panorama photographing or a sensor for CT photographing depending on a kind of image that is to be photographed.

For example, the sensor portion 20 may be fixedly mounted through a plurality of frames BK1, BK2, and BK3 fixed to the lower portion of one side of the rotating portion 100.

The X-ray source portion 10 is provided at the lower portion of the other side of the rotating portion 100. In detail, the X-ray source portion 10 is axially coupled to a coupling hole 110$h$3 formed at the lower portion of the other side of the rotating portion 110.

The X-ray source portion 10 is a portion generating an X-ray and irradiating the generated X-ray toward the sensor portion 20, a head H of a subject to be examined is positioned between the X-ray source portion 10 and the sensor portion 20, and the X-ray irradiated from the X-ray source portion 10 passes through the head H of the subject to be examined and is then detected through the sensor portion 20, such that X-ray photographing for the head H of the subject to be examined may be performed.

The rotating portion 100 as described above may be configured by assembling a plurality of frames to each other, and may be configured to include, for example, an upper frame 110 and a lower frame 120.

The upper frame 110 is provided with a rectangular hole 110$h$1 through which the shaft 1 penetrates, and the lower frame 120 is coupled to the upper frame 110 so as to cover a lower portion of the upper frame 110.

Therefore, the shaft 1 is in a state in which it penetrates through the rectangular hole 110$h$1, and the rotating portion 100 may be slid through the moving means 300 in the X-ray irradiation direction without interference with the shaft 1.

Figure 2:
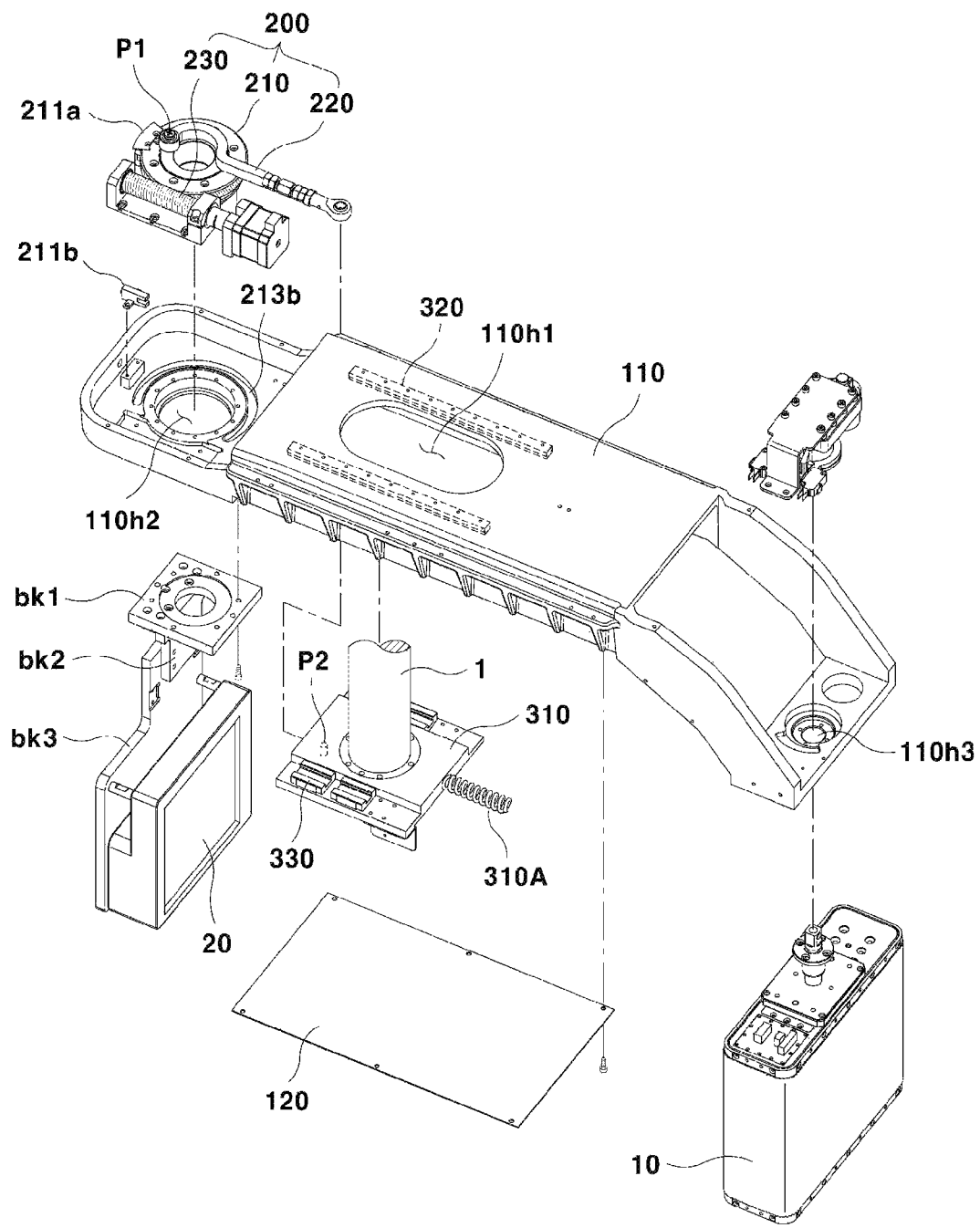
FIG. 2 is an exploded perspective view illustrating the X-ray photographing apparatus according to an exemplary embodiment of the present invention.

The moving means 300 is a portion allowing the rotating portion 100 to be slid in the X-ray irradiation direction. In detail, as illustrated in FIGS. 2 and 3, the moving means 300 supports the rotating portion 100 so that the rotating portion 100 is relatively movable in the X-ray irradiation direction with respect to the shaft 1.

Figure 3:
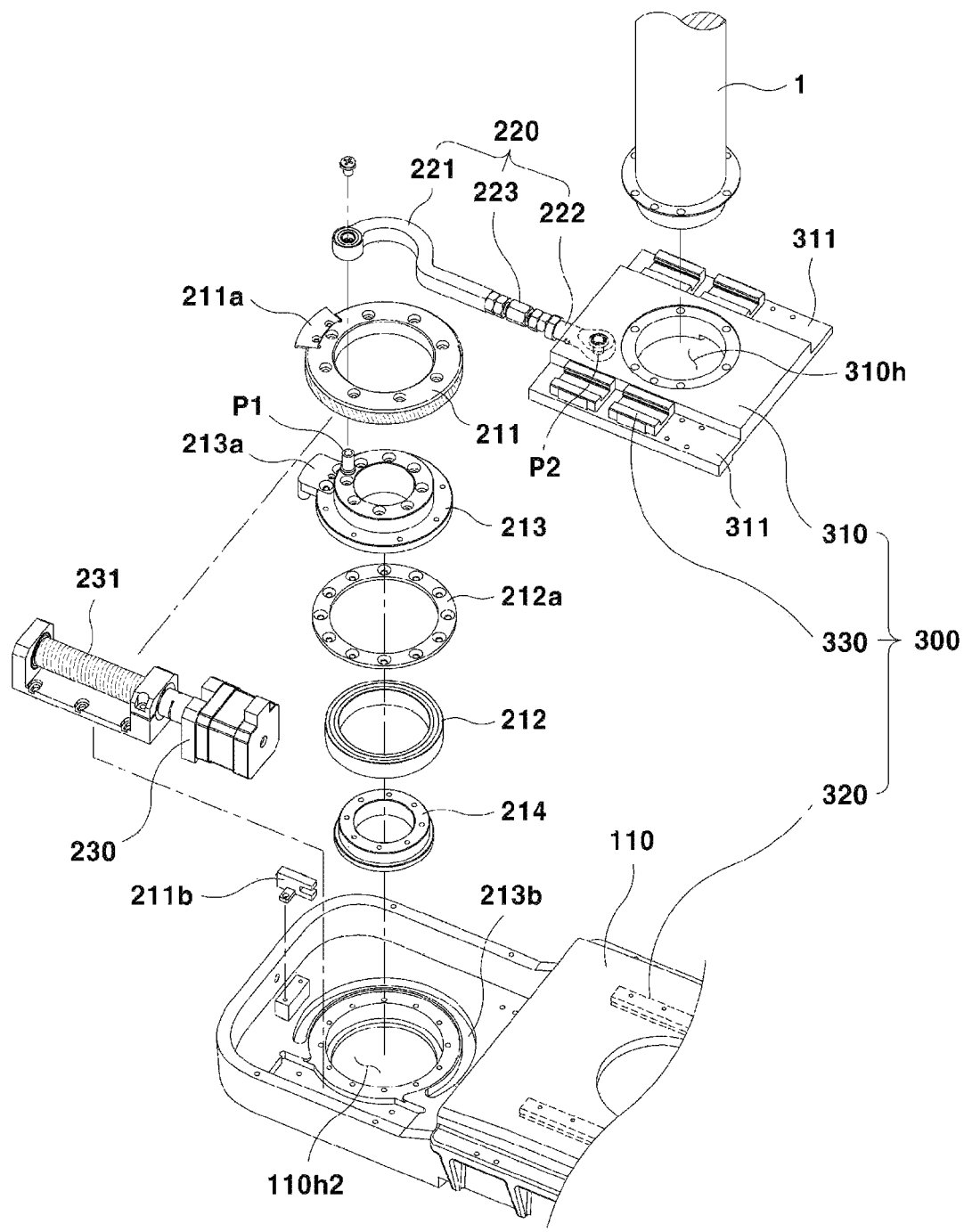
FIG. 3 is an exploded perspective view illustrating some components of the X-ray photographing apparatus according to an exemplary embodiment of the present invention.

In detail, as illustrated in FIG. 3, the moving means 300 may be configured to include a fixed plate 310 fixed to a lower end portion of the shaft 1, guide rails 320 provided on any one of one side of the fixed plate 310 and one side of an inner portion of the rotating portion 100, and guide blocks 330 provided on the other of one side of the fixed plate 310 and one side of the inner portion of the rotating portion 100 and rail-coupled to the guide rails 320.

The fixed plate 310 is a plate-shaped member, and a coupling hole 310$h$ into which an end portion of the shaft 1 is inserted and fixedly coupled is formed at a central portion of the fixed plate 310.

For example, the guide blocks 330 may be provided on both sides of an upper surface of the fixed plate 310, and the guide rails 320 may be provided on one side of the inner portion of the upper frame 110 corresponding to both sides of the upper surface of the fixed plate 310.

The guide blocks 330 may be configured in the plural in a slid direction of the rotating portion 100. For example, as illustrated in FIG. 2, the guide blocks 330 may be installed in an array of 2×2, and may be, preferably, LM guide blocks.

The guide rails 320 may be a pair of LM rails formed on a bottom surface of the upper frame 110 corresponding to both sides of the rectangular hole 110$h$1 formed in the upper frame 110.

Meanwhile, step portions 311 extended in a length direction so that the guide blocks 330 are mounted thereon may be formed on both sides of an upper surface of the fixed plate 310. The step portion 311 may allow the fixed plate 310 and an inner surface of the upper frame 110 to be in close contact with each other to reduce an entire volume of the rotating portion 100.

As described above, the rotating portion 100 may be relatively slid in the X-ray irradiation direction with respect to the shaft 1 through the moving means 300 configured to include the fixed plate 310, the guide blocks 330, and the guide rails 320.

Meanwhile, the fixed plate 310 may be configured to be elastically pulled toward the X-ray source portion 10. To this end, an elastic member 310A elastically pulling the fixed plate 310 toward the X-ray source portion 10 is provided.

The elastic member 310A may be formed of, for example, an elastic body such as a spring, having one end connected to one surface of the fixed plate 310 and the other end connected to one point of an inner portion of the upper frame 110 constituting the rotating portion 100, as illustrated in FIG. 2.

The elastic member 310A elastically pulls the fixed plate 310 toward the X-ray source portion 10 to serve to prevent fine movement of the fixed plate 310.

According to the configuration of the rotating portion 100 as described above, the rotating portion 100 may be slid in the X-ray irradiation direction through the moving means 300, and the movement of the fixed plate 310 is prevented through the elastic member 310A.

Then, the actuating portion 200 will be described.

The actuating portion 200 adjusts a magnification power by changing an interval between the sensor portion 20 and the head H of the subject to be examined in a state in which an interval between the X-ray source portion 10 and the sensor portion 20 is maintained.

Figure 4:
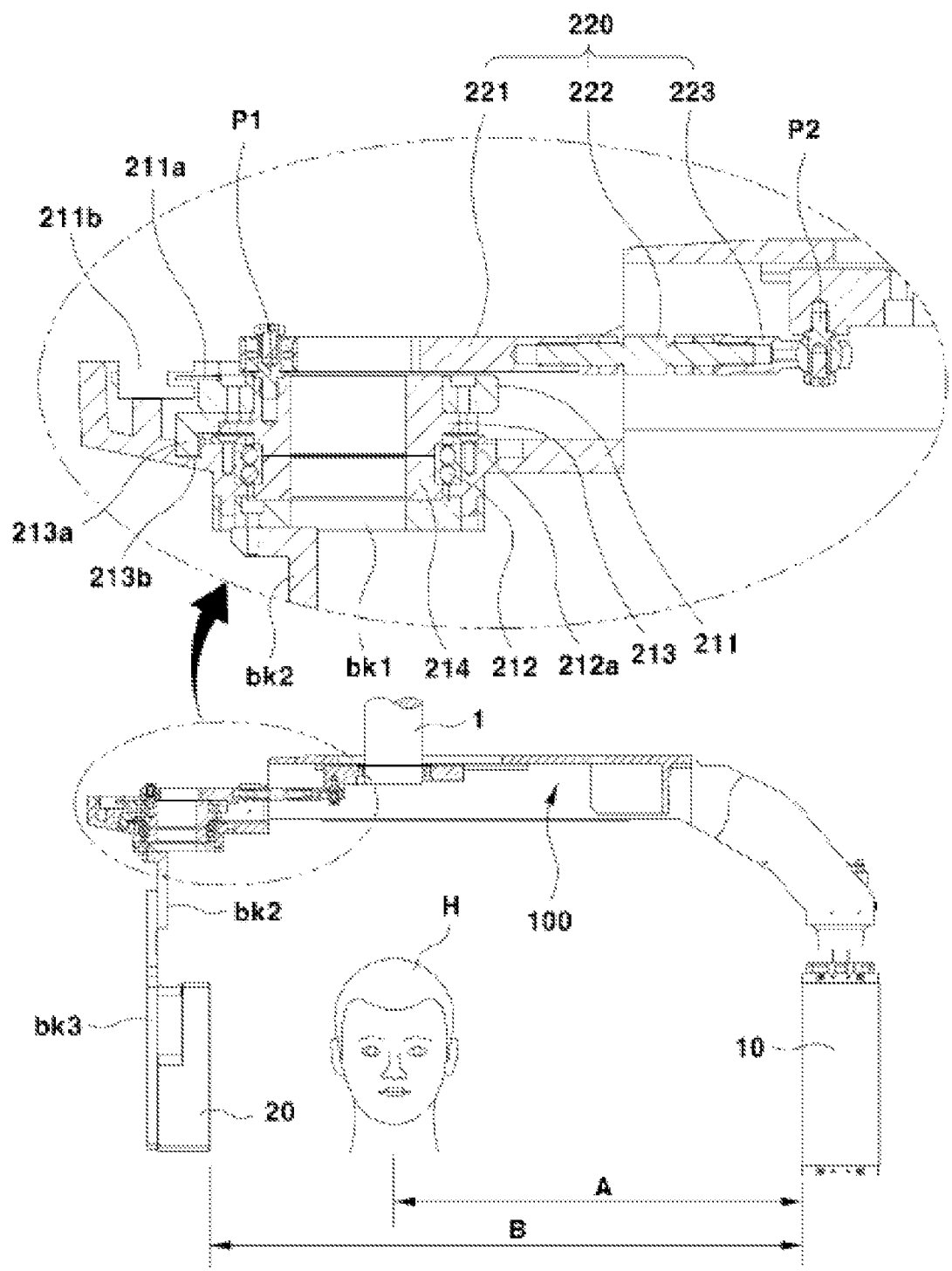
FIG. 4 is a cross-sectional view illustrating the X-ray photographing apparatus according to an exemplary embodiment of the present invention.

As illustrated in FIG. 4, the magnification power is defined by a ratio of a distance A between the head H of the subject to be examined, which is a photographing target, and the X-ray source portion 10 to a distance B between the X-ray source portion 10 and the sensor portion 20.

In detail, the actuating portion 200 is actuated so as to move the rotating portion 100 to one side position (see FIGS. 5A and 5B) at which the rotating portion 100 is maximally moved in one side direction, the other side position (see FIGS. 6A and 6B) at which the rotating portion 100 is maximally moved in the other side direction, and an intermediate position (see FIGS. 9A to 10B), which is any position in a section between one side position and the other side position.

That is, the actuating portion 200 adjusts the magnification power by changing the interval between the sensor portion 20 and the head H of the subject to be examined by the movement of the rotating portion 100 to any one of one side portion, the other side portion, and the intermediate position in the state in which the interval between the X-ray source portion 10 and the sensor portion 20 is maintained, in a state in which a position of the head H of the subject to be examined is fixed.

The magnification power adjusted by the actuating portion 200 may be variously adjusted depending on a photographing mode. For example, the actuating portion 200 may change the interval between the sensor portion 20 and the head H of the subject to be examined so that the magnification power is adjusted to a magnification power for panorama photographing or a magnification power for CT photographing.

As a specific example, in the state in which a position of the head H of the subject to be examined is fixed, when the rotating portion 100 is moved to one side position in the state in which the interval between the X-ray source portion 10 and the sensor portion 20 is maintained, the magnification power may be adjusted to the magnification power for CT photographing, and when the rotating portion 100 is moved to the other side position in the state in which the interval between the X-ray source portion 10 and the sensor portion 20 is maintained, the magnification power may be adjusted to the magnification power for panorama photographing.

In addition, the actuating portion 200 may change the interval between the sensor portion 20 and the head H of the subject to be examined so that the magnification power is adjusted to any one of a plurality of CT photographing magnification powers.

As a specific example, in the state in which a position of the head H of the subject to be examined is fixed, when the rotating portion 100 is moved to one side position in the state in which the interval between the X-ray source portion 10 and the sensor portion 20 is maintained, the magnification power may be adjusted to a first magnification power of a plurality of magnification powers at which CT photographing may be performed, and when the rotating portion 100 is moved to the other side position in the state in which the interval between the X-ray source portion 10 and the sensor portion 20 is maintained, the magnification power may be adjusted to a second magnification power of the plurality of magnification powers at which the CT photographing may be performed.

In addition, the actuating portion 200 may change the interval between the sensor portion 20 and the head H of the subject to be examined so that the magnification power is adjusted to any one of a plurality of panorama photographing magnification powers.

As a specific example, in the state in which a position of the head H of the subject to be examined is fixed, when the rotating portion 100 is moved to one side position in the state in which the interval between the X-ray source portion 10 and the sensor portion 20 is maintained, the magnification power may be adjusted to a first magnification power of a plurality of magnification powers at which panorama photographing may be performed, and when the rotating portion 100 is moved to the other side position in the state in which the interval between the X-ray source portion 10 and the sensor portion 20 is maintained, the magnification power may be adjusted to a second magnification power of the plurality of magnification powers at which the panorama photographing may be performed.

Meanwhile, since the X-ray source portion 10 and the sensor portion 20 are fixed to one side and the other side of the rotating portion 100, respectively, and face each other in the state in which a predetermined interval therebetween is maintained, photographing may be performed even in a state in which the rotating portion 100 is positioned at the intermediate position, and the actuating portion 200 may position the rotating portion 100 at the intermediate position to variously adjust the magnification power.

That is, the actuating portion 200 selectively moves the rotating portion 100 to any one intermediate position in the section between one side position and the other side position to variously adjust the magnification power.

As described above, in the case in which the actuating portion 200 moves the rotating portion 100 to any one intermediate position in the section between one side position and the other side position to adjust the magnification power, the actuating portion 200 may adjust the magnification power to a provisional magnification power by changing the interval between the sensor portion 20 and the head H of the subject to be examined into a preset interval, and then adjust the magnification power to a final magnification power by changing the interval between the sensor portion 20 and the head H of the subject to be examined so as to become wide or narrow in consideration of a size of the head H of the subject to be examined, which will be described in detail in a description for an X-ray photographing method according to the present exemplary embodiment.

As described above, the actuating portion 200 adjusting the magnification power by changing the interval between the sensor portion 20 and the head H of the subject to be examined may be configured to include a rotating unit 210 provided in the rotating portion 100, a link unit 220 having one end connected to one point on a radius of rotation of the rotating unit 210 in a hinge manner and the other end connected to one point of the moving means 300 in a hinge manner, and a driving unit 230 rotating the rotating unit 210, as illustrated in FIGS. 2 and 3.

As illustrated in FIG. 3, the rotating unit 210 is configured to include a first gear 211, and the driving unit 230 is configured to include a second gear 231 engaged with the first gear 211.

The first gear 211 may be a worm wheel gear, and the second gear 231 may be a worm gear.

In detail, the rotating unit 210 is provided on a hollow hole 110h2 formed in one side of the upper frame 110 of the rotating portion 110. In more detail, the rotating unit 210 is configured to include a bearing 212 having an outer ring coaxially fixedly mounted on an inner circumferential surface of the hollow hole 110h2, an upper switching shaft 213 coaxially mounted on an inner ring of the bearing 212 and having a ring shape, a lower switching shaft 214 coaxially mounted beneath the inner ring of the bearing 212 and having a ring shape, and the first gear 211 coupled to an upper outer circumferential surface of the upper switching shaft 213.

The rotating unit 210 configured as described above is rotatably supported in a state in which the upper switching shaft 213, the lower switching shaft 214, and the first gear 211 are coupled integrally with one another by the bearing 212.

The bearing 212 may be prevented from being separated from the hollow hole 110h2 by a bearing holder block 212a.

The driving unit 230 is installed at one side of the rotating portion 100 so as to be adjacent to the first gear 211 of the rotating unit 210, and may be formed of, for example, a rotating motor having a rotation driving shaft, and the second gear 231 may be coaxially fixed to the rotation driving shaft and be configured to be engaged with the first gear 211.

Therefore, when the second gear 231 rotates in a forward or reverse direction, the first gear 211 engaged with the second gear 231 rotates in the forward or reverse direction.

The link unit 220, which is a portion performing a link operation so that the interval between the sensor portion 20 and the head H of the subject to be examined may be changed by driving of the driving unit 230, has one end connected to one point on the radius of rotation of the rotating unit 210 in the hinge manner and the other end connected to one point of the moving means 300 in the hinge manner.

The link unit 220 may be configured to include a first body 221 connected to one point on the radius of rotation of the rotating unit 210 in the hinge manner, a second body 222 connected to one point of the moving means 300 in the hinge manner, and a length adjuster 223 having one end fastened to the first body 221 in a left-handed or right-handed manner and the other end fastened to the second body 222 in an opposite manner to that of the first body 221.

In detail, a first hinge-pin P1 to which one end of the link unit 220 is to be connected in the hinge manner is provided at one point on a radius of rotation of the upper switching shaft 213 of the rotating unit 210, and a second hinge-pin P2 to which the other end of the link unit 220 is to be connected in the hinge manner is provided at one point on a lower surface of the fixed plate 310 constituting the moving means 300.

Therefore, in the case in which the upper switching shaft 213 rotates by the driving unit 230, the link unit 220 connected to each of the first hinge pin P1 and the second hinge pin P2 in the hinge manner is interlocked and is link-driven, such that the rotating portion 100 may be slid to one side or the other side.

The length adjuster 223 may adjust a distance between the first body 221 and the second body 222 to precisely adjust an initial position of a rotating body.

The first body 221 constituting one side of the link unit 220 may be configured to include a portion bent in a semi-circular shape, which is to prevent a cable, or the like, disposed to penetrate through the center of the rotating unit 210 so as to be extended to the sensor portion 20 from interfering with the link unit 220.

Meanwhile, a sensing bracket 211a is fixedly provided at one side of the first gear 211 of the rotating unit 210, a sensing sensor 211b is provided at a position corresponding to that of the sensing bracket 211a, and an initial position of the upper switching shaft 213 may be sensed by the sensing bracket 211a and the sensing sensor 211b. A groove portion in which the sensing bracket 211a is to be mounted may be formed in a portion of the first gear 211.

In addition, an angle limiting stopper 213a having a '¬' shape is provided at a portion of the upper switching shaft 213 of the rotating unit 210, a C-shaped groove portion 213b is formed at a portion of the rotating portion 100 corresponding to an end portion of the angle limiting stopper 213a, and a rotation range of the upper switching shaft 213 may be limited by the angle limiting stopper 213a and the C-shaped groove portion 213b. A groove portion in which the angle limiting stopper 213a is to be mounted may be formed in a portion of the upper switching shaft 213.

An X-ray photographing method according to an exemplary embodiment of the present invention may be implemented through the X-ray photographing apparatus as described above, and adjusts the magnification power by changing the interval between the sensor portion 20 and the head H of the subject to be examined in the state in which the interval between the X-ray source portion 10 and the sensor portion 20 facing each other is maintained. Meanwhile, the sensor portion 20 may be configured to perform the panorama photographing or the CT photographing.

In adjusting the magnification power by changing the interval between the sensor portion 20 and the head H of the subject to be examined by the X-ray photographing method according to the present exemplary embodiment, the interval between the sensor portion 20 and the head H of the subject to be examined may be changed so that the magnification power is, for example, any one of the magnification power for the panorama photographing and the magnification power for the CT photographing.

Meanwhile, in adjusting the magnification power by changing the interval between the sensor portion 20 and the head H of the subject to be examined by the X-ray photographing method according to the present exemplary embodiment, the interval between the sensor portion 20 and the head H of the subject to be examined may be changed so that the magnification power is, for example, any one of the plurality of panorama photographing magnification powers.

Meanwhile, in adjusting the magnification power by changing the interval between the sensor portion 20 and the head H of the subject to be examined by the X-ray photographing method according to the present exemplary embodiment, the interval between the sensor portion 20 and the head H of the subject to be examined may be changed so that the magnification power is, for example, preferably, any one of the plurality of CT photographing magnification powers.

Hereinafter, photographing examples of performing X-ray photographing using the X-ray photographing apparatus and method as described above will be described.

PHOTOGRAPHING EXAMPLE 1

Figure 5A:
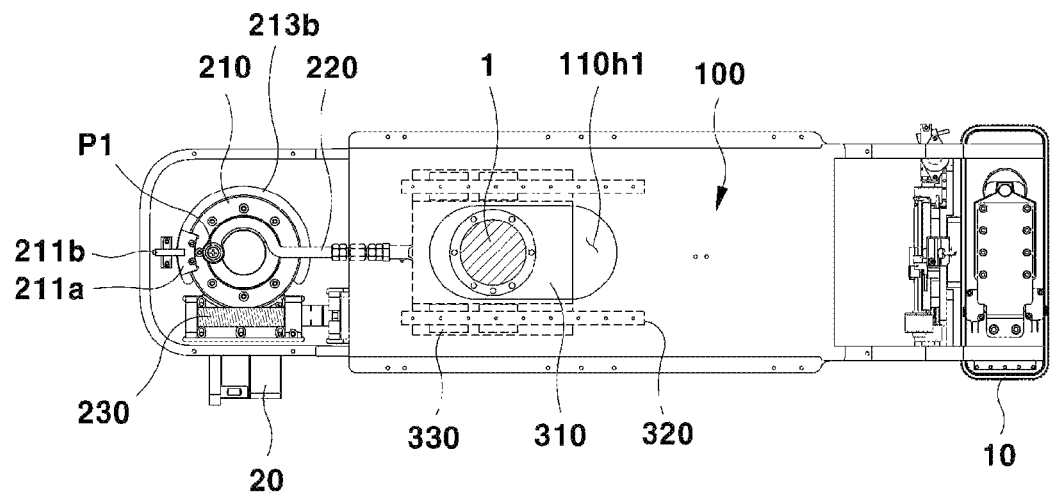
FIGS. 5A and 5B are views illustrating a case in which a rotating portion of the X-ray photographing apparatus according to an exemplary embodiment of the present invention moves to one side position to perform computerized tomography (CT) photographing.
Figure 5B:
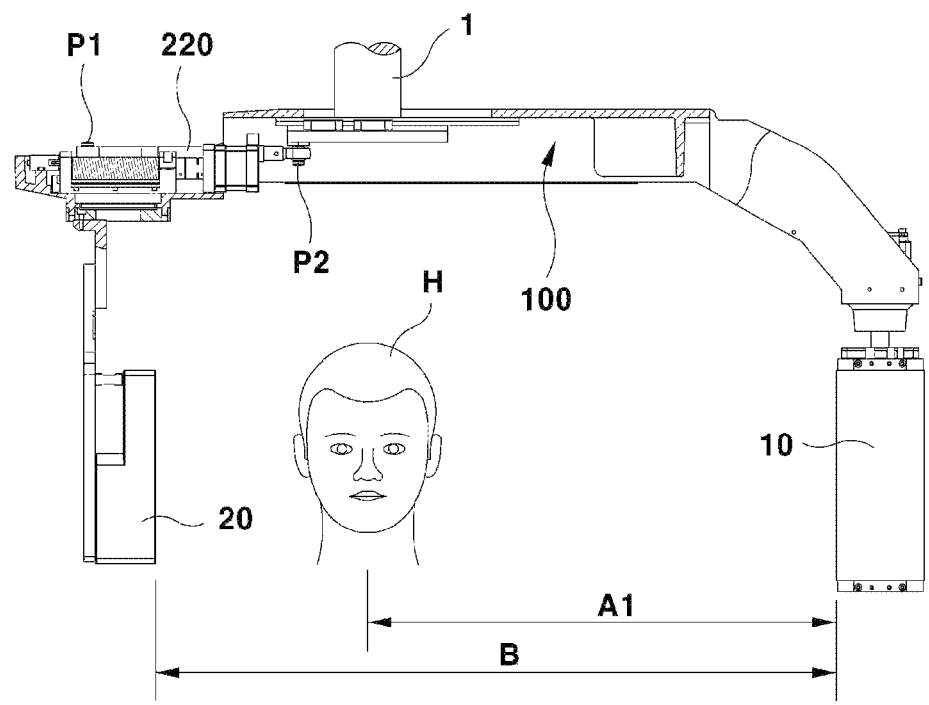
Figure 6A:
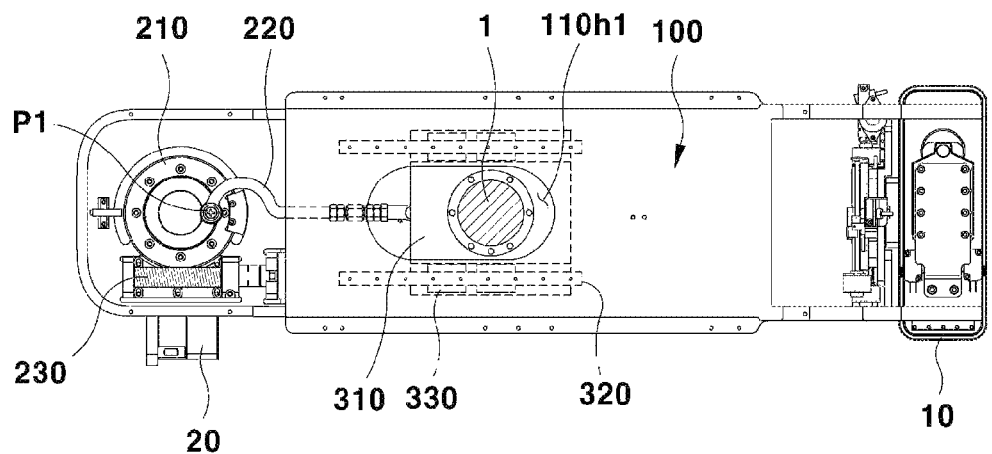
FIGS. 6A and 6B are views illustrating a case in which the rotating portion of the X-ray photographing apparatus according to an exemplary embodiment of the present invention moves to the other side position to perform panorama photographing.
Figure 6B:
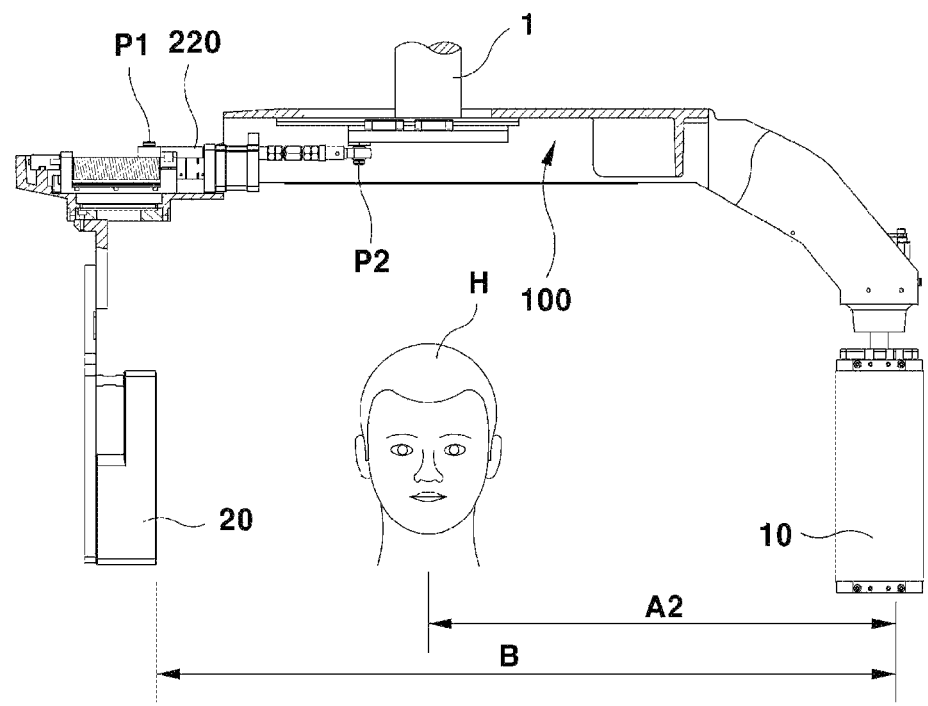

One Side Position-Magnification Power for CT Photographing, the Other Side Position-Magnification Power for Panorama Photographing The rotating portion 100 moves to one side position as illustrated in FIGS. 5A and 5B or moves to the other side position as illustrated in FIGS. 6A and 6B to adjust the magnification power, thereby making it possible to perform X-ray photographing.

As illustrated in FIGS. 5A and 5B, when the rotating portion 100 moves to one side position, a distance ratio of a distance between the head H of the subject to be examined, which is the photographing target, and the X-ray source portion 10 to a distance between the X-ray source portion 10 and the sensor portion 20 becomes A1:B, such that the magnification power may be adjusted to the magnification power for the CT photographing.

As illustrated in FIGS. 6A and 6B, when the rotating portion 100 moves to the other side position, a distance ratio of a distance between the head H of the subject to be examined, which is the photographing target, and the X-ray source portion 10 to a distance between the X-ray source portion 10 and the sensor portion 20 becomes A2:B, such that the magnification power may be adjusted to the magnification power for the panorama photographing.

As described above, the rotating portion 100 moves to one side position or the other side position, such that the magnification power may be adjusted to the magnification power for the CT photographing or the panorama photographing and photographing may then be performed.

PHOTOGRAPHING EXAMPLE 2

Figure 7A:
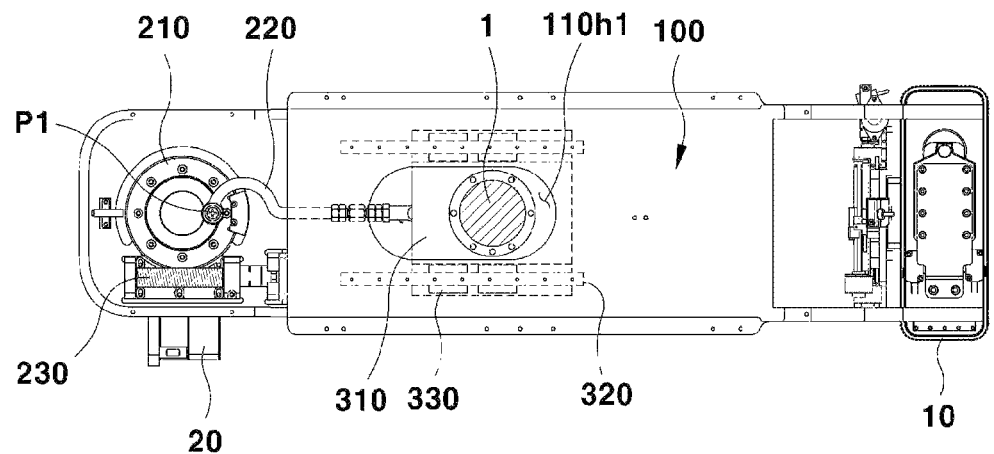
FIGS. 7A and 7B are views illustrating a case in which the rotating portion of the X-ray photographing apparatus according to an exemplary embodiment of the present invention moves to one side position to adjust a magnification power to a first magnification power.
Figure 7B:
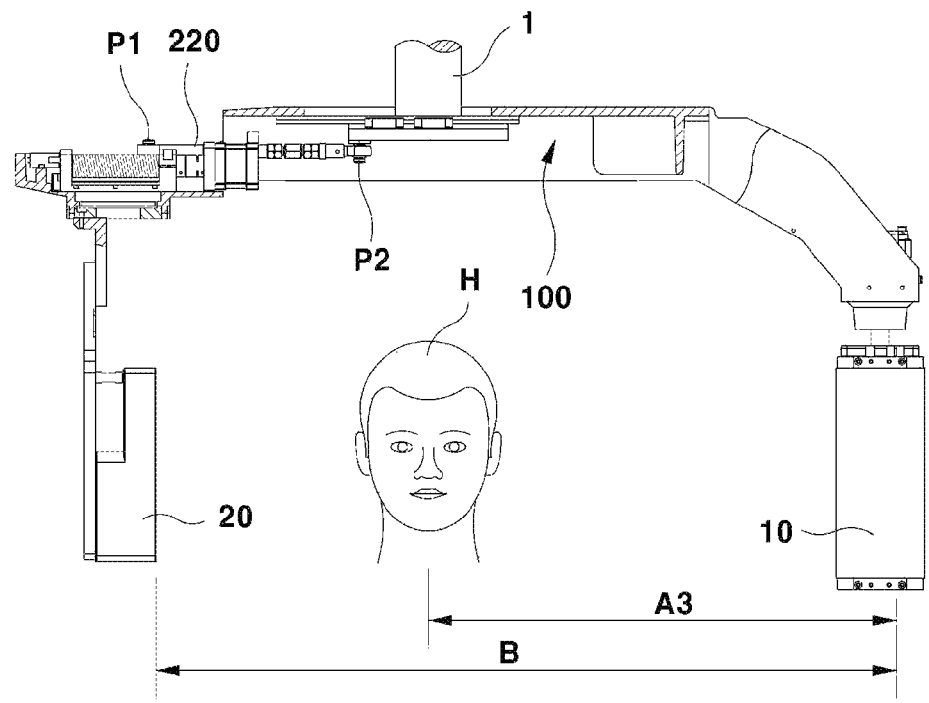
Figure 8A:
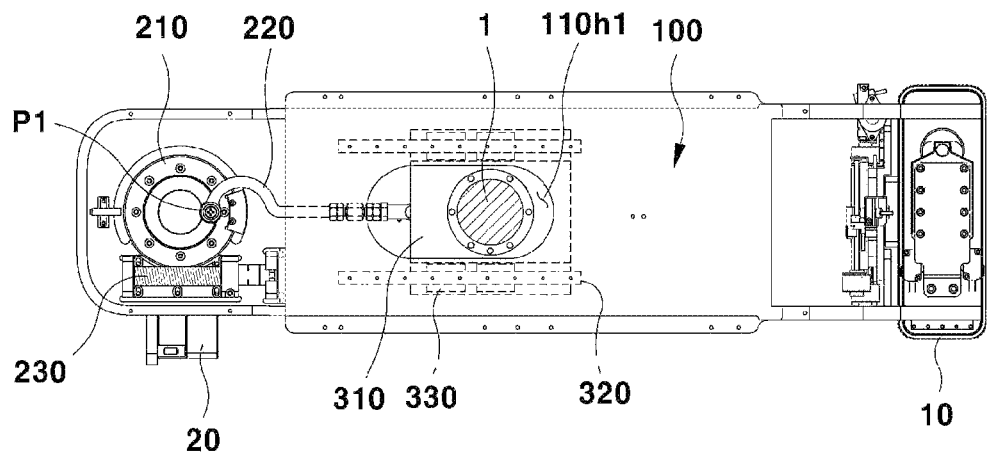
FIGS. 8A and 8B are views illustrating a case in which the rotating portion of the X-ray photographing apparatus according to an exemplary embodiment of the present invention moves to the other side position to adjust a magnification power to a second magnification power.
Figure 8B:
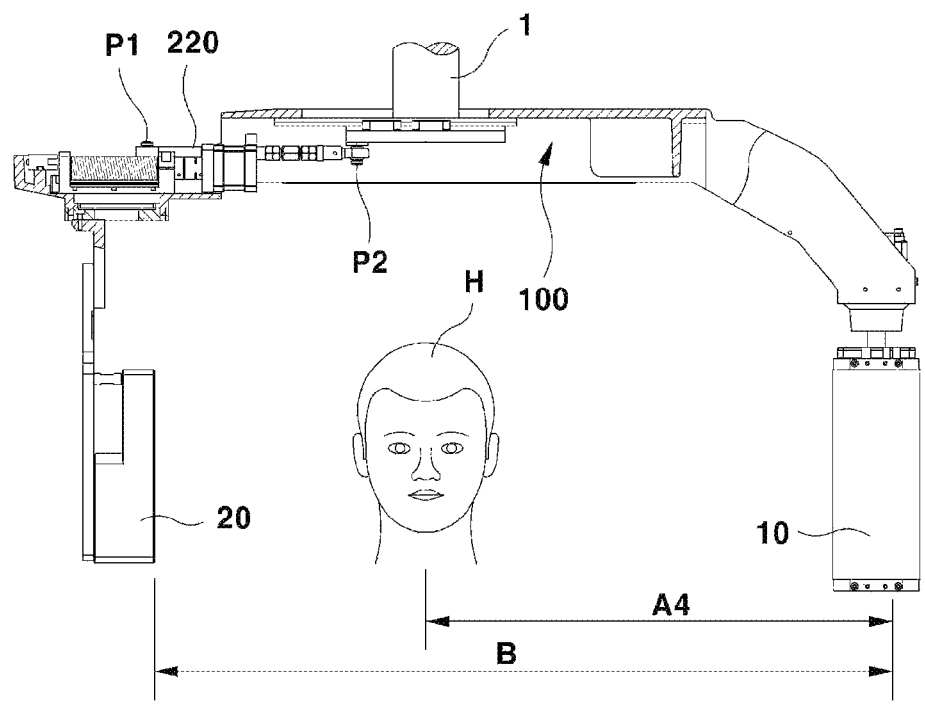

One Side Position-First Magnification Power, the Other Side Position-Second Magnification Power The rotating portion 100 moves to one side position as illustrated in FIGS. 7A and 7B or moves to the other side position as illustrated in FIGS. 8A and 8B to adjust the magnification power, thereby making it possible to perform X-ray photographing.

As illustrated in FIGS. 7A and 7B, when the rotating portion 100 moves to one side position, a distance ratio of a distance between the head H of the subject to be examined, which is the photographing target, and the X-ray source portion 10 to a distance between the X-ray source portion 10 and the sensor portion 20 becomes A3:B, such that the magnification power may be adjusted to the first magnification power, which is any one of various magnification powers for X-ray image photographing.

As illustrated in FIGS. 8A and 8B, when the rotating portion 100 moves to the other side position, a distance ratio of a distance between the head H of the subject to be examined, which is the photographing target, and the X-ray source portion 10 to a distance between the X-ray source portion 10 and the sensor portion 20 becomes A4:B, such that the magnification power may be adjusted to the second magnification power, which is a magnification power different from the first magnification power among the various magnification powers for X-ray image photographing.

As described above, the rotating portion 100 moves to one side position or the other side position, thereby making it possible to perform the X-ray image photographing at the first magnification power or perform the X-ray image photographing at the second magnification power.

For example, an operator may perform the X-ray image photographing at the first magnification power or perform the X-ray image photographing at the second magnification power. In addition, the operator may continuously perform the X-ray image photographing two times at the first magnification power and the second magnification power, and then select and use an image having better quality, of two images obtained by performing the X-ray image photographing two times.

Meanwhile, the X-ray image photographing may be CT image photographing or panorama image photographing, and for example, the CT image photographing may be performed at the first magnification power and the CT image photographing may be performed at the second magnification power or the panorama image photographing may be performed at the first magnification power and the panorama image photographing may be performed at the second magnification power.

The first magnification power and the second magnification power may be varied depending on a photographing environment or a kind of photographing.

PHOTOGRAPHING EXAMPLE 3

Figure 9A:
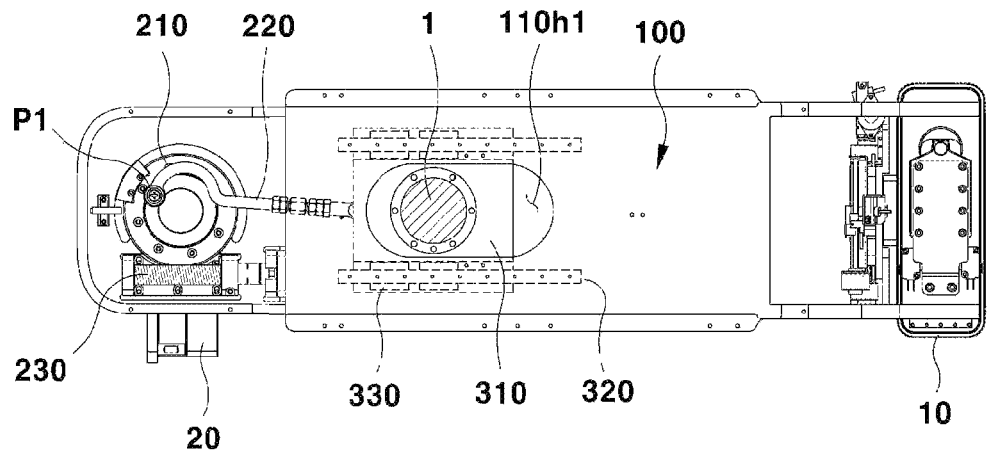
FIGS. 9A and 9B are views illustrating a case in which the rotating portion of the X-ray photographing apparatus according to an exemplary embodiment of the present invention moves to a first intermediate position.
Figure 9B:
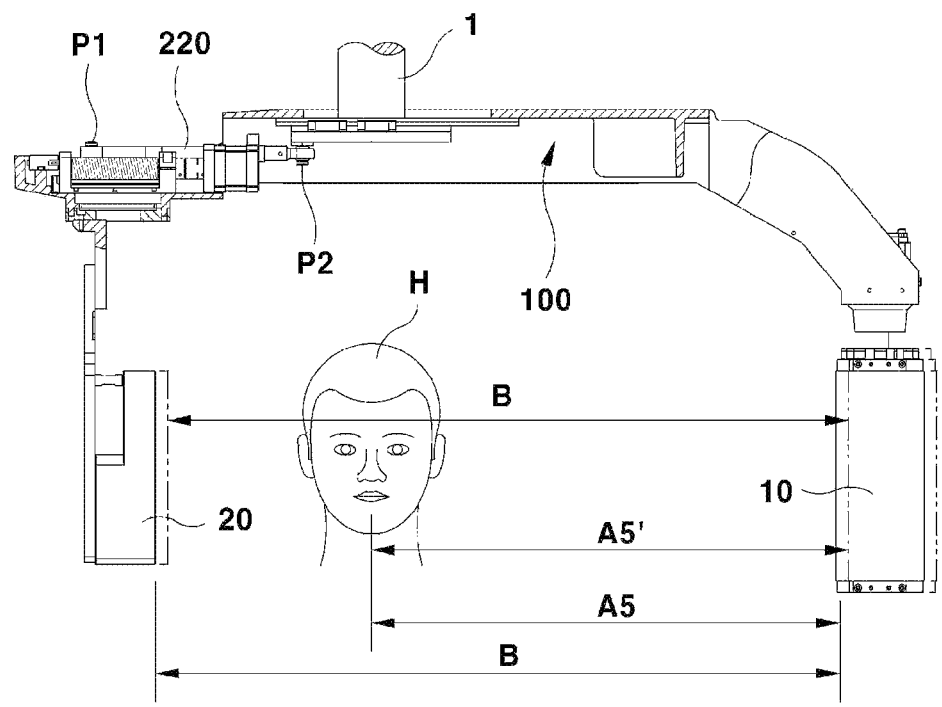
Figure 10A:
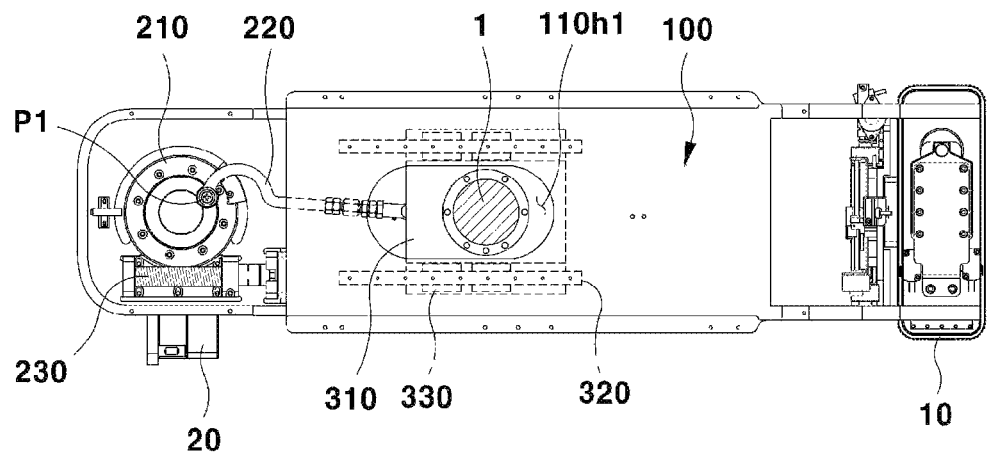
FIGS. 10A and 10B are views illustrating a case in which the rotating portion of the X-ray photographing apparatus according to an exemplary embodiment of the present invention moves to a second intermediate position.
Figure 10B:
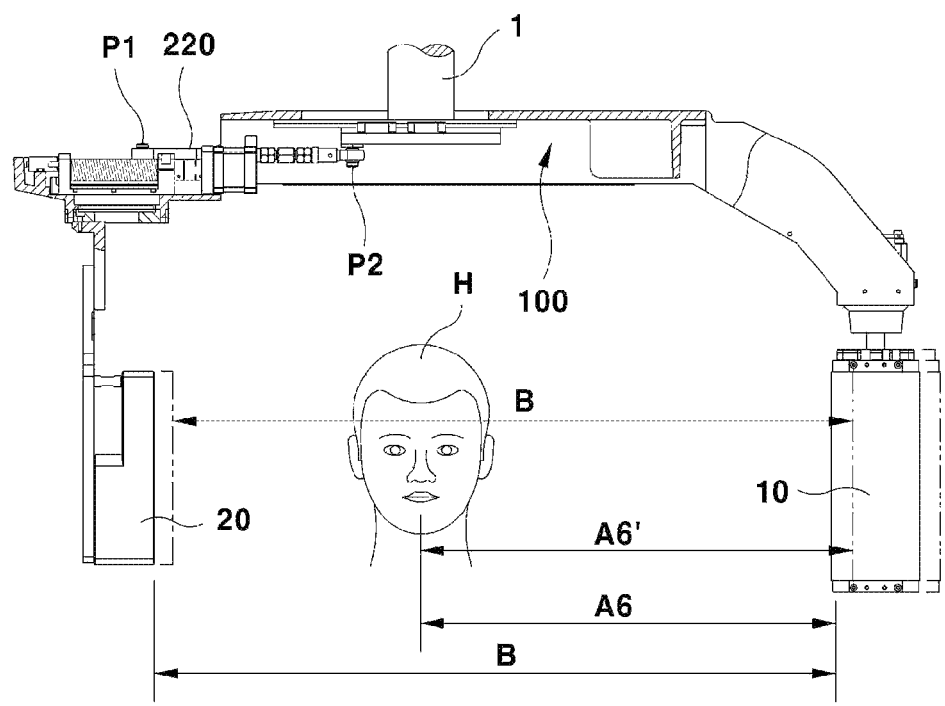

First Intermediate Position-First Magnification Power, Second Intermediate Position-Second Magnification Power The rotating portion 100 moves to a first intermediate position close to one side position as illustrated in FIGS. 9A and 9B or moves to a second intermediate position close to the other side position as illustrated in FIGS. 10A and 10B to adjust the magnification power, thereby making it possible to perform X-ray photographing.

As illustrated in FIGS. 9A and 9B, as the interval between the sensor portion 20 and the head H of the subject to be examined is adjusted to a preset interval, when the rotating portion 100 moves to the first intermediate position, a distance ratio of a distance between the head H of the subject to be examined, which is the photographing target, and the X-ray source portion 10 to a distance between the X-ray source portion 10 and the sensor portion 20 becomes A5:B, such that the magnification power is adjusted to a provisional magnification power (A5:B) before being adjusted to a first magnification power (A5':B), which is a final magnification power.

After the magnification power is adjusted to the provisional magnification power (A5:B) as described above, an operator finely adjusts a position of the rotating portion 100 in consideration of a size of the head H of the subject to be examined to adjust the magnification power to the final magnification power (A5':B).

For example, in the case in which a size of the head H is small as in the case of a child, the position of the rotating portion 100 is finely adjusted and moved so that the sensor portion 20 becomes closer to the head H of the subject to be examined, thereby making it possible to adjust the provisional magnification power to be the first magnification power, which is the final magnification power.

In addition, for example, in the case of a subject to be examined of which a size of a head H is larger than a standard size of the head H, the position of the rotating portion 100 is finely adjusted and moved so that the sensor portion 20 becomes more distant from the head H of the subject to be examined, thereby making it possible to adjust the provisional magnification power to be the first magnification power, which is the final magnification power.

Meanwhile, a decision of whether or not the size of the head H of the subject to be examined is smaller than the standard size of the head H and a decision of whether or not the size of the head H of the subject to be examined is larger than the standard size of the head H may be made by a separate head size deciding means or be made by a decision of the operator, and the decision by the separate head size deciding means or the operator may be made on the basis of human body size information registered in Size Korea (http://sizekorea.kats.go.kr).

As described above, a manner of adjusting the magnification power to the provisional magnification power and then adjusting the magnification power to the first magnification power by finely adjusting the rotating portion 100 may be equally or similarly applied to a case of adjusting the second magnification power.

That is, the magnification power may be adjusted to a provisional magnification power (A6:B), and be then adjusted to a second magnification power (A6':B) by finely adjusting the rotating portion 100.

Although the present invention has been mainly described for exemplary embodiments with reference to the accompanying drawings, it is apparent to those skilled in the art that various modifications may be made without departing from the spirit and scope of the present invention. Therefore, the scope of the present invention is to be interpreted by the claims stated to include these many modifications.

The invention claimed is:
1. An X-ray photographing apparatus comprising:
a rotating portion including an X-ray source portion and a sensor portion facing each other and provided at a shaft through a moving means so as to be movable in an X-ray irradiation direction; and
an actuating portion adjusting a magnification power by changing an interval between the sensor portion and a head of a subject to be examined in a state in which an interval between the X-ray source portion and the sensor portion is maintained.
2. The X-ray photographing apparatus of claim 1, wherein the actuating portion adjusts the magnification power to a provisional magnification power by changing the interval between the sensor portion and the head of the subject to be examined into a preset interval, and then adjusts the magnification power to a final magnification power by changing the interval between the sensor portion and the head of the subject to be examined so as to become wide or narrow in consideration of a size of the head of the subject to be examined.

3. The X-ray photographing apparatus of claim 1, wherein the actuating portion adjusts the magnification power by moving the rotating portion so that the rotating portion moves to and is positioned at any one of one side position, the other side position, and an intermediate position corresponding to any position in a section between one side position and the other side position.
4. The X-ray photographing apparatus of claim 1, wherein the actuating portion changes the interval between the sensor portion and the head of the subject to be examined so that the magnification power is adjusted to a magnification power for panorama photographing or a magnification power for computerized tomography (CT) photographing.
5. The X-ray photographing apparatus of claim 1, wherein the moving means is configured so that the rotating portion is relatively movable with respect to the shaft.
6. The X-ray photographing apparatus of claim 5, wherein the moving means is configured to include a fixed plate provided at the shaft, guide rails provided on any one of one side of the fixed plate and one side of an inner portion of the rotating portion, and guide blocks provided on the other of one side of the fixed plate and one side of the inner portion of the rotating portion and rail-coupled to the guide rails.
7. The X-ray photographing apparatus of claim 6, wherein the guide blocks are provided on both sides of an upper surface of the fixed plate, the guide rails are provided on one side of the inner portion of the rotating portion corresponding to both sides of the upper surface of the fixed plate, and step portions extended in a length direction so that the guide blocks are mounted thereon are formed on both sides of the upper surface of the fixed plate.
8. The X-ray photographing apparatus of claim 1, wherein the actuating portion is configured to include:
a rotating unit provided in the rotating portion;
a link unit having one end connected to one point on a radius of rotation of the rotating unit in a hinge manner and the other end connected to one point of the moving means in a hinge manner; and
a driving unit rotating the rotating unit.
9. The X-ray photographing apparatus of claim 8, wherein the rotating unit is configured to include a first gear, and the driving unit is configured to include a second gear engaged with the first gear.
10. The X-ray photographing apparatus of claim 8, wherein the rotating unit is configured to include a sensing bracket provided at one side thereof and a sensing sensor sensing a rotation position of the sensing bracket depending on rotation of the rotating unit.
11. The X-ray photographing apparatus of claim 8, wherein the rotating unit is configured to include an angle limiting stopper provided at one side thereof and a C-shaped groove portion formed at a portion of the rotating portion corresponding to the angle limiting stopper.
12. The X-ray photographing apparatus of claim 5, wherein an elastic member elastically pulling the fixed plate toward the X-ray source portion is provided.
13. The X-ray photographing apparatus of claim 8, wherein the link unit is provided with a length adjusting portion.
14. The X-ray photographing apparatus of claim 8, wherein one side of the link unit is bent in a semi-circular shape.
15. The X-ray photographing apparatus of claim 8, wherein the link unit is configured to include:
a first body connected to one point on the radius of rotation of the rotating unit in the hinge manner;

a second body connected to one point of the moving means in the hinge manner; and a length adjuster having one end fastened to the first body in a left-handed or right-handed manner and the other end fastened to the second body in an opposite manner to that of the first body and adjusting a distance between the first body and the second body.

16. The X-ray photographing apparatus of claim 1, wherein the rotating portion is configured to include an upper frame provided with a rectangular hole through which the shaft penetrates and a lower frame covering a lower portion of the upper frame, and the actuating portion is configured to include a rotating unit provided on a hollow hole formed in one side of the rotating portion, a link unit having one end connected to one point on a radius of rotation of the rotating unit in a hinge manner and the other end connected to one point of the moving means in a hinge manner, and a driving unit rotating the rotating unit.

17. The X-ray photographing apparatus of claim 16, wherein the rotating unit is configured to include a bearing mounted on the hollow hole, an upper switching shaft mounted on an inner portion of the bearing, a lower switching shaft mounted beneath the inner portion of the bearing, and a first gear coupled to an upper outer circumferential surface of the upper switching shaft, and the sensor portion is fixedly mounted at a lower portion of one side of the rotating portion.

18. An X-ray photographing method comprising:

a step of adjusting a magnification power by changing an interval between a sensor portion and a head of a subject to be examined in a state in which an interval between an X-ray source portion and the sensor portion facing each other is maintained.

19. The X-ray photographing method of claim 18, wherein the step of adjusting the magnification power includes:

a first adjusting step of adjusting the magnification power to a provisional magnification power by changing the interval between the sensor portion and the head of the subject to be examined into a preset interval; and a second adjusting step of adjusting the magnification power to a final magnification power by changing the interval between the sensor portion and the head of the subject to be examined so as to become wide or narrow in consideration of a size of the head of the subject to be examined.

20. The X-ray photographing method of claim 18, wherein the interval between the sensor portion and the head of the subject to be examined is changed so that the magnification power is adjusted to any one of a magnification power for panorama photographing and a magnification power for CT photographing.

* * * * *